(12) United States Patent
Ansmann et al.

(10) Patent No.: US 8,158,680 B2
(45) Date of Patent: Apr. 17, 2012

(54) ESTER OF HEXYLDECANOL HAVING SHORT-CHAINED FATTY ACIDS

(75) Inventors: Achim Ansmann, Erkrath (DE); Markus Dierker, Duesseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 95 days.

(21) Appl. No.: 12/597,658

(22) PCT Filed: Apr. 17, 2008

(86) PCT No.: PCT/EP2008/003067
§ 371 (c)(1), (2), (4) Date: Oct. 26, 2009

(87) PCT Pub. No.: WO2008/131863
PCT Pub. Date: Nov. 6, 2008

(65) Prior Publication Data
US 2010/0130609 A1    May 27, 2010

(30) Foreign Application Priority Data
Apr. 26, 2007  (EP) .................................. 07008476

(51) Int. Cl.
*A61K 31/23* (2006.01)
*C07C 53/00* (2006.01)

(52) U.S. Cl. ........................................ 514/552; 554/230

(58) Field of Classification Search ............... 514/552
See application file for complete search history.

(56) References Cited

U.S. PATENT DOCUMENTS

| | | | |
|---|---|---|---|
| 5,656,664 A | 8/1997 | O'Lenick, Jr. | |
| 6,391,287 B1 | 5/2002 | Baldo et al. | |
| 6,689,345 B2 * | 2/2004 | Jager | 424/64 |
| 2006/0099160 A1 * | 5/2006 | Dumousseaux | 424/64 |
| 2006/0171910 A1 * | 8/2006 | Ricard et al. | 424/70.1 |
| 2010/0298432 A1 * | 11/2010 | Ansmann et al. | 514/552 |

FOREIGN PATENT DOCUMENTS

JP    10279527    10/1998

OTHER PUBLICATIONS

Gerald Kirchner, et al., Resolution of Racemic Mixtures via Lipase Catalysis in Organic Solvents, J. Am. Chem. Soc. 1985, 107, 7072-7076.
R. Pinol, et al., Structure-activity Studies of Ferroelectric and Antiferroelectric Imine Ligands and Their Square-Planar Complexes, Liquid Crystals, vol. 31, No. 9, Sep. 2004, 1293-1303.

* cited by examiner

*Primary Examiner* — Brandon Fetterolf
*Assistant Examiner* — Shirley V Gembeh
(74) *Attorney, Agent, or Firm* — Diehl Servilla LLC

(57) ABSTRACT

The present invention relates to the use of one or more esters of 2-hexyldeconal having fatty acids of the general formula (I) R1-COOH, wherein R1 is a linear or branched, saturated or unsaturated alkyl radical having 1 to 6 carbon atoms, in and/or for the production of cosmetic and/or pharmaceutical preparations.

4 Claims, No Drawings

ESTER OF HEXYLDECANOL HAVING SHORT-CHAINED FATTY ACIDS

CROSS REFERENCE TO RELATED APPLICATIONS

This application is the National Stage entry of PCT/EP2008/003067, filed Apr. 17, 2008, which claims priority to European Patent application number 07008476.9, filed Apr. 26, 2007, both of which are incorporated herein by reference in their entireties.

FIELD OF THE INVENTION

The invention relates to esters of hexyldecanol with short-chain fatty acids and their use in cosmetic and/or pharmaceutical preparations.

BACKGROUND OF THE INVENTION

In the field of cosmetic preparations for skin care and hair care, and also in the field of pharmaceutical preparations, a large number of requirements are imposed by the consumer: apart from the cleaning and care effects, which determine the intended use, value is placed on such differing parameters as highest possible dermatological compatibility, good refatting properties, elegant appearance, optimum sensory impression and storage stability.

Preparations which are used for the cleaning and care of the human skin and hair generally comprise, besides a series of surface-active substances, in particular oil bodies and water. The oil bodies/emollients used are, for example, hydrocarbons, ester oils and also vegetable and animal oils/fats/waxes. In order to meet the high requirements of the market with regard to sensory properties and optimum dermatological compatibility, new oil bodies are being continually developed and tested.

Esters of hexyldecanol with fatty acids are known, for example, from U.S. Pat. No. 6,391,287 (L'Oréal), where hexyldecyl caprylate (=octanoate), hexydecyl laurate (=dodecanoate), hexydecyl palmitate (=hexadecanoate) and hexyldecyl stearate (=octadecanoate) are described as cosolubilizers for bicyclic aromatic compounds. Furthermore, the compound hexyldecyl 2-ethylhexanoate is sold by Kokyu Alcohol Co. Ltd under the trade name ICEH.

U.S. Pat. No. 5,656,664 describes esters of alpha-methyl-branched alcohols with acids and their use as "conditioning agents" for the skin. A disadvantage of these esters is their unsatisfactory sensory properties and also their low stability, in particular upon thermal stress.

In the Journal of the American Society, vol. 107, No. 24 from 1985 on p. 7073 in Scheme II as Example 11, G. Kirchner et al. describe an ester of 2-hexadecanol and butanoic acid.

There is still a need for new oil bodies which have a more flexible use spectrum (e.g. compatibility with further cosmetic ingredients) and also meet the high requirements placed on the sensory properties. Of particular interest are oil bodies which produce a feeling referred to as "light" on the skin. The distributability and speadability on the skin are of great importance. The modern consumer requires that oil bodies and the preparations produced therefrom generate a soft skin feel and that the skin feels cared for. A further requirement of modern raw materials for cosmetic and/or pharmaceutical preparations is that they can be obtained on the basis of renewable, vegetable raw materials. Of particular interest are compounds that are characterized by advantageous sensory properties, and also of particular interest are compounds which are storage-stable, in particular storage-stable at elevated temperatures.

It was an object of the present invention to provide novel substances which are suitable for cosmetic and/or pharmaceutical preparations, in particular as oil bodies/emollients and produce a sensorially particularly "light" skin feel. Furthermore, these substances should be obtainable on the basis of renewable vegetable raw materials.

DETAILED DESCRIPTION OF PREFERRED EMBODIMENTS

Surprisingly, it has been found that esters of 2-hexyldecanol with short-chain fatty acids are suitable for cosmetic and/or pharmaceutical preparations, and can be used in these preparations especially as sensorially particularly advantageous oil bodies.

The esters according to the invention are characterized by advantageous sensory properties and by increased stability compared with the compounds known in the prior art.

The invention provides the use of one or more esters of 2-hexyldecanol with fatty acids of the general formula (I)

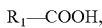

where $R_1$ is a linear or branched, saturated or unsaturated alkyl radical having 1 to 6 carbon atoms, in and/or for the production of cosmetic and/or pharmaceutical preparations.

The esters according to the invention are suitable in particular as oil bodies in cosmetic and/or pharmaceutical preparations.

The invention further provides esters of 2-hexyldecanol with fatty acids of the general formula (I)

where $R_1$ is a linear or branched, saturated or unsaturated alkyl radical having 1 to 6 carbon atoms, with the exception of (R)-2-hexyldecylbutanoic acid ester.

2-Hexyldecanol is used as alcohol component of the ester. 2-Hexyldecanol (synonymously 2-hexyl-1-decanol or 2-hexyldecyl alcohol) is commercially available as e.g. under the trade name Eutanol®G 16 (Cognis Deutschand GmbH & Co KG) or as Exxal® 16 (Exxon Chemical Company). 2-Hexyldecanol is a so-called Guerbet alcohol which is available by self-condensation of (primary) alcohols under the influence of sodium or copper at elevated temperature and pressure. 2-Hexyldecanol has a chiral carbon atom and can thus be present as the R and also as the S enantiomer, as any desired mixture of the two enantiomers, and also as racemate. Esters of 2-hexyldecanol within the context of this invention include both the esters of the respective enantiomers, mixtures of these enantiomers, and also the corresponding racemates. Commercially available 2-hexyldecanol is generally the racemate.

Fatty acids of the general formula (I)

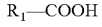

where $R_1$ is a linear or branched, saturated or unsaturated alkyl radical having 1 to 6 carbon atoms, are used as fatty acid component.

The following are suitable, for example, as $R_1$: methyl, ethyl, propyl, isopropyl, [=1-methylethyl], propenyl, isobutyl [=2-methylpropyl], sec-butyl [=1-methylpropyl], tert-butyl [=1,1-dimethylethyl], but-2-enyl, but-3-enyl, but-1-enyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, 1-pentenyl, 2-pentenyl, 3-pentenyl, 4-pentenyl, hexyl, 1-methylpentyl, 2-methylpentyl, 3-methylpentyl, 4-methylpentyl, 1-ethylbutyl, 2-ethylbutyl, 3-ethylbutyl, 1-hexenyl, 2-hexenyl, 3-hexenyl, 4-hexenyl, 5-hexenyl.

In one preferred embodiment of the invention, a fatty acid of the general formula (I) is used in which $R_1$ is a linear or branched, saturated alkyl radical having 1 to 6 carbon atoms, particularly preferably a linear, saturated alkyl radical having 1 to 6 carbon atoms.

Particularly suitable esters within the context of the invention are
2-hexyldecylacetic acid ester ($R_1$=$CH_3$),
2-hexyldecylpropanoic acid ester ($R_1$=$C_2H_5$),
2-hexyldecylpentanoic acid ester ($R_1$=$C_4H_9$),
2-hexyldecylhexanoic acid ester ($R_1$=$C_5H_{11}$),
2-hexyldecylheptanoic acid ester ($R_1$=$C_6H_{13}$).

Esters to be used particularly advantageously within the context of the invention are
2-hexyldecylacetic acid ester ($R_1$=$CH_3$),
2-hexyldecylpropanoic acid ester ($R_1$=$C_2H_5$),
2-hexyldecylbutanoic acid ester ($R_1$=$C_3H_7$),
2-hexyldecylpentanoic acid ester ($R_1$=$C_4H_9$),
2-hexyldecylhexanoic acid ester ($R_1$=$C_5H_{11}$),
2-hexyldecylheptanoic acid ester ($R_1$=$C_6H_{13}$).

PREPARATION

The esters according to the invention are prepared by esterification methods known to the person skilled in the art. Thus, for example, the fatty acid can be esterified together with the hexyldecanol in the presence of a catalyst.

Both the alcohol components and also the fatty acid component can be obtained from vegetable raw materials, such as, for example, palm kernel oil or coconut oil. Consequently, the esters according to the invention are obtainable entirely on the basis of renewable raw materials.

Use in Cosmetic and/or Pharmaceutical Preparations

Surprisingly, it has been established that the esters according to the invention are particularly suitable for the production of cosmetic preparations, and they are suitable in particular as oil bodies/emollients and/or consistency regulators in cosmetic preparations. The esters according to the invention are furthermore suitable for the production of pharmaceutical preparations, where the according to the invention are used as technical auxiliaries, such as e.g. oil bodies. The esters according to the invention can serve for the production of cosmetic preparations, such as, for example, hair shampoo, hair lotions, foam baths, shower baths, creams, gels, lotions, alcoholic and aqueous/alcoholic solutions, emulsions, wax/fatty masses, stick preparations, powders or salves. These compositions can also comprise, as further auxiliaries and additives, mild surfactants, oil bodies, emulsifiers, pearlescent waxes, consistency regulators, thickeners, superfatting agents, stabilizers, polymers, silicone compounds, fats, waxes, lecithins, phospholipids, biogenic active ingredients, UV sun protection factors, antioxidants, deodorants, antiperspirants, antidandruff agents, film formers, swelling agents, insect repellants, self-tanning agents, tyrosine inhibitors (depigmentation agents), hydrotropes, solubilizers, preservatives, perfume oils, dyes and the like. Preference is given to the use of the esters according to the invention as oil bodies.

The esters according to the invention can be used in cosmetic formulations as so-called "light emollients" in order to establish special properties, such as e.g. spreading behavior or volatility. The esters according to the invention furthermore permit the production of viscosity-stable cosmetic formulations. Compared with the 1-methyl-branched esters of the prior art, the esters according to the invention are characterized by improved sensory properties and also by increased stability, in particular upon thermal stress.

The esters according to the invention can be used either individually or in any desired mixtures with one another.

EXAMPLES

Preparation Example 1 mol of hexanoic acid (116 g) hexanoic acid, 1.1 mol (297 g) of 2-hexyldecanol (Guerbitol®16) and 0.22 g of Fascat® 2001 (tin oxalate) were combined and heated to 240° C. on the water separator for 3 h. The product was then distilled over a 30 cm column (153-168° C. at 0.8 mbar). The product is produced as a colorless and odorless oil.

What is claimed is:

1. A method of producing cosmetic and/or pharmaceutical preparations comprising adding to a cosmetic and/or pharmaceutical base, one or more esters wherein the ester is the esterification product of 2-hexyldecanol with fatty acids of the general formula (I)

$$R_1-COOH \qquad (I)$$

where $R_1$ is a linear or branched, saturated or unsaturated alkyl group having 1 to 6 carbon atoms.

2. The method of claim 1 wherein said one or more esters are incorporated in said cosmetic and/or pharmaceutical preparation as an oil body.

3. An ester wherein the ester is the esterification product of 2-hexyldecanol with fatty acids of the general formula (I)

$$R_1-COOH \qquad (I)$$

where $R_1$ is a linear or branched, saturated or unsaturated alkyl group having 1 to 6 carbon atoms, provided that (R)-2-hexyldecylbutanoic acid ester is excluded.

4. The ester of claim 3, selected from the group consisting of 2-hexyldecylacetic acid ester, 2-hexyldecylpropanoic acid ester, 2-hexyldecylpentanoic acid ester, 2-hexyldecylhexanoic acid ester and 2-hexyldecylheptanoic acid ester.

* * * * *